United States Patent [19]

Ogden et al.

[11] 4,252,027
[45] Feb. 24, 1981

[54] METHOD OF DETERMINING THE PLATING PROPERTIES OF A PLATING BATH

[75] Inventors: Cameron A. Ogden, Thousand Oaks; Dennis M. Tench, Ventura; John T. White, Oxnard, all of Calif.

[73] Assignee: Rockwell International Corporation, El Segundo, Calif.

[21] Appl. No.: 76,058

[22] Filed: Sep. 17, 1979

[51] Int. Cl.$^3$ .......................... G01N 3/08; C25D 1/02
[52] U.S. Cl. .......................................... 73/826; 204/9
[58] Field of Search ..................... 204/195 R, 9, 3, 4, 204/1 T; 73/826, 789

[56] References Cited

U.S. PATENT DOCUMENTS

| | | | |
|---|---|---|---|
| 1,268,465 | 6/1918 | Huggins | 204/9 |
| 2,568,713 | 9/1951 | Brenner | 204/195 R |
| 4,043,876 | 8/1977 | Hambling | 204/9 |
| 4,102,770 | 7/1978 | Moriarty | 204/212 |

*Primary Examiner*—T. M. Tufariello
*Attorney, Agent, or Firm*—H. Fredrick Hamann; Craig O. Malin

[57] ABSTRACT

A band of material is formed by plating the material onto a cylindrical cathode sandwiched between a pair of insulating end pieces and is supported in a plating bath spaced a short distance from an anode. The cathode is rotated about its axis to provide uniform, reproducible mass transport to the plating surface. In order to determine the tensile properties of the plated material, the band is removed from the cathode and pulled apart in a tensile machine. During tensile testing, the band is held using a pair of pins and clevis, or it is formed into a strip and gripped in a standard fixture. In order to determine the stress condition of the plated material, the band is cut open and its change in diameter measured.

5 Claims, 3 Drawing Figures

METHOD OF DETERMINING THE PLATING PROPERTIES OF A PLATING BATH

BACKGROUND OF THE INVENTION

1. Field of the Invention

This invention relates to the field of plating and particularly to the field of quality control of plating baths.

2. Description of the Prior Art

Quality control of plating baths is a difficult problem because plating is a complex process involving many ingredients in the plating bath. Small fluctuations in the concentration of ingredients at the electrode surface, especially organic additives, significantly affect brightness, morphology, and mechanical properties of the deposit.

One method used to control the quality of a plating bath is to form a test specimen from plated material and then tensile test the specimen to determine the mechanical properties of the material. The major problem encountered in forming tensile test specimens is to provide uniform, reproducible solution mass transport to the surface being plated. Previously, some combination of conventional stirring, gas bubbling, electrolyte recirculation, or ultrasonic agitation had been relied upon to transport solution species to the electrode. Because agitation thus provided is neither reproducible nor uniform, results of tensile testing the deposited material have not been reliable.

Additional problems are more intimately associated with the sample geometry. Tensile test specimens are generally cut or stamped from larger foils plated on flat stainless steel panels, or are plated directly in the test configuration on masked panels. Since deposits tend to fall off smooth substrates during plating, the steel panels are often roughened to promote sample adhesion. Irregularities in such cut or stamped edges and rough surface defects thus produced can initiate premature failure, yielding unreliable results. Since specimens are generally thin ($\leq 0.05$ mm), distortion of the sample near the specimen grips can also be significant, so that many samples fail within the grips. Finally, sample alignment is critical for such thin samples.

SUMMARY OF THE INVENTION

It is an object of the invention to provide an apparatus and a method for forming a band of plating under conditions of well-defined solution mass transport.

It is an object of the invention to provide an apparatus and a method for use in determining the tensile properties of a plated deposit.

It is an object of the invention to provide an apparatus and a method for use in determining the stress condition of a plated deposit.

According to the invention, a cathode is formed by sandwiching a metallic cylinder between a pair of insulating end pieces. The cathode is supported in a plating bath adjacent to an anode in the bath. The cathode is rotated about its axis to provide uniform, reproducible mass transport to the surface being plated.

Depending upon the type of material being plated, the deposited band can be removed by either sliding it off the cylindrical cathode or by dissolving the cylindrical cathode in a suitable solvent (for example, sodium hydroxide) for dissolving an aluminum cathode).

In the preferred embodiment of the invention, the band is pulled apart in a tensile machine in order to determine the tensile properties of the deposited material. This can be accomplished by opening or flattening the band to form a strip which can then be held in the grips of a tensile machine, or by using a pair of pins and clevises to hold the band while it is pulled apart.

The apparatus and method can be used to form bands of electroless deposits by using an electroless bath (such as electroless nickel) and eliminating the anode.

These and other objects and features of the invention will be apparent from the following detailed description, taken with reference to the accompanying drawings.

DESCRIPTION OF THE PREFERRED EMBODIMENT

Figure 1:
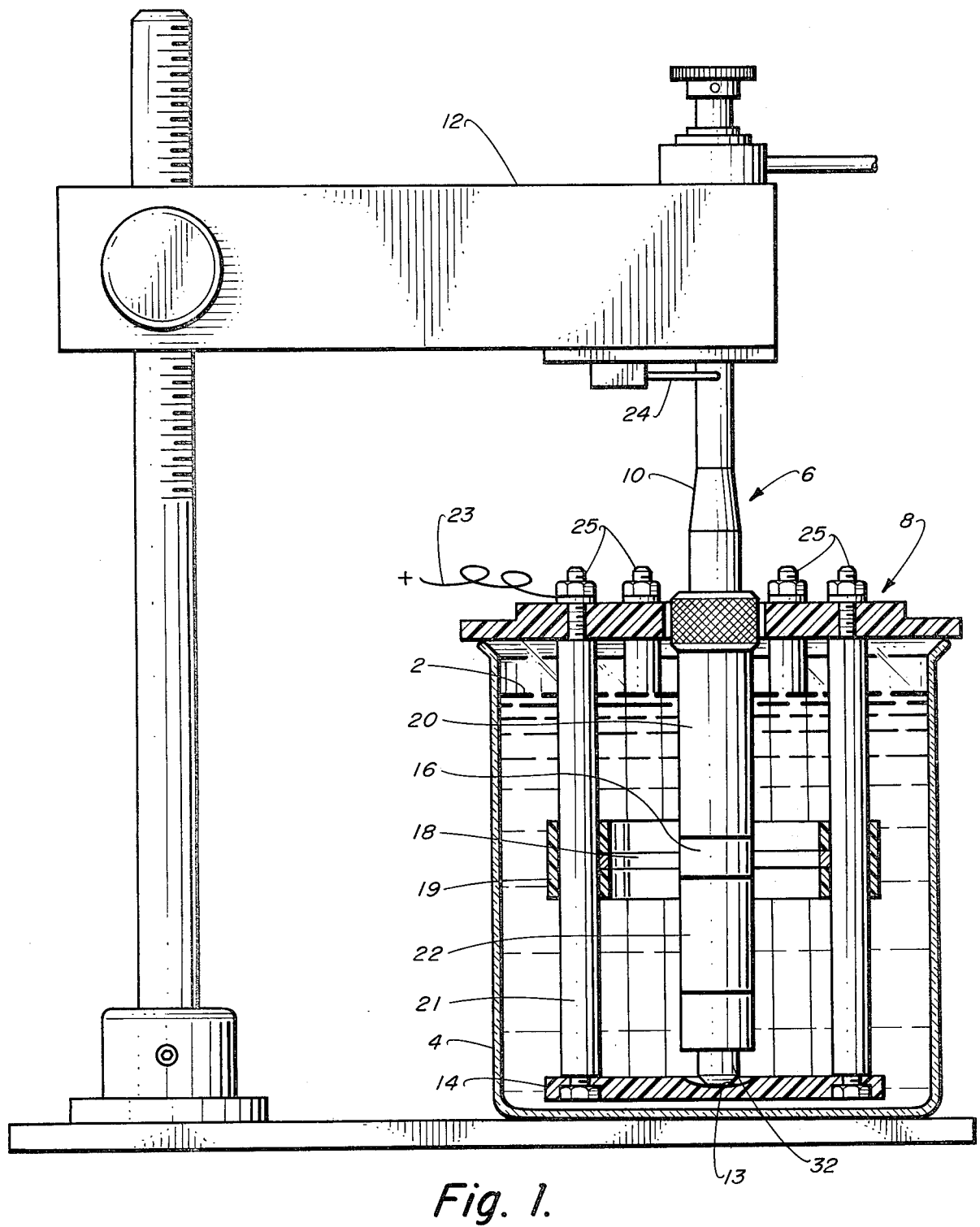
FIG. 1 is a perspective view of an assembled cathode, anode, and rotator being used to test a plating bath sample.

FIG. 1 shows the apparatus of the invention being used to electroplate a copper band from a copper pyrophosphate electrolyte 2 contained in glass beaker 4. Rotating cathode assembly 6 is positioned inside anode support assembly 8. The top of cathode assembly 6 is machined to fit into a commercially available rotator such as model ASR-2 Rotator from the Pine Instrument Company. The bottom of cathode assembly 6 fits into centering hole 13 in bottom plate 14 of anode support assembly 8.

The cathode upon which metal is deposited is metal cylinder 16 which is positioned in the center of ring anode 18. Electric contact is made to cathode 16 by silver-graphite brush 24 installed in the rotator head so that is bears against shaft 10. Anode 18 is shielded in plastic casing 19 and secured by posts 21 to bottom piece 14. Anode 18 is connected to a source of anode current 23 via insulated bus connector posts 25. When a suitable plating potential is applied across cylinder 16 and anode 18, copper is plated onto cathode 16 in the shape of a band. Non-conductive plastic end pieces 20, 22 are provided on both sides of cathode 16 so that metal is plated only on cylinder 16, thus limiting the width of the band to the width of cathode 16.

Figure 2:
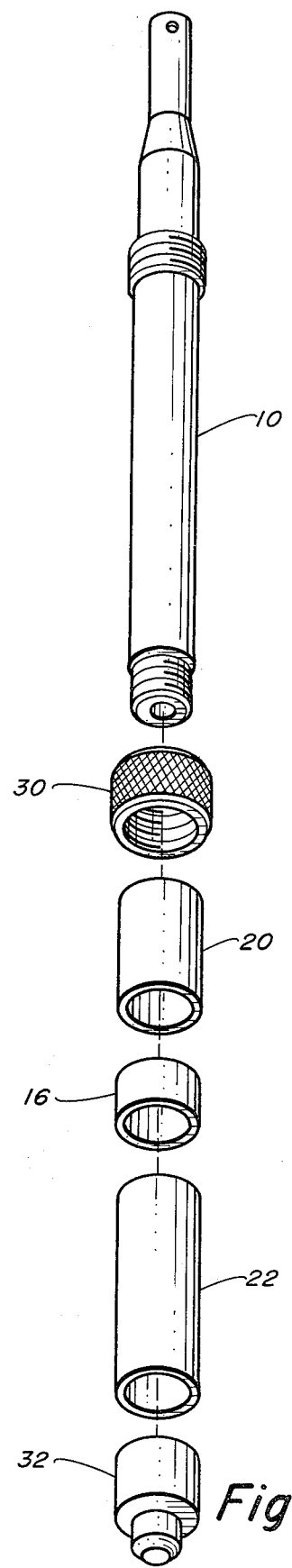
FIG. 2 is an exploded view of a cathode assembly according to a preferred embodiment of the invention.

Cathode assembly 6 is shown in detail in FIG. 2. The cathode is a cylindrical metal sleeve 16 which is sandwiched between plastic sleeves 20, 22 of the same diameter (+0.05 mm, −0 mm) on electrode shaft 10, then secured top and bottom by knurled nut 30 and threaded plastic knob 32. The top of electrode shaft 10 is beveled and threaded on an inside diameter to mate precisely with rotator motor bearing assembly 12. Plastic knob 32 is beveled to fit into centering hole 13 in anode assembly 8. Two close-fitting shields cover the entire assembly in 1500 ml pyrex cell 4. Although not shown in FIG. 2, cell 4 is generally water jacketed to maintain a constant temperature.

Electrode shaft 10 may be fabricated from stainless steel such as type 304, and the non-conductive parts from a fluorocarbon polymer such as Kel-F or Teflon. The anode and bus connector may be fabricated from any suitable anode material. Cathode metal cylinder 16 may be fabricated from stainless steel or aluminum.

Since only inert fluorocarbon or anode material is exposed to the test solution (except for cathode cylinder 16 which is exposed for only a very short time as plating begins) solution contamination is minimized. This is important because tests have shown that deposit properties can be strongly affected by low concentrations of bath impurities.

For example, freshly prepared copper pyrophosphate baths produced deposits with variable tensile properties until low level impurities were removed from the solution by pre-electrolysis (dummying) or sample plating. About five hours of pre-electrolysis was required before the mechanical properties of the deposits became constant. Similarly, when a stainless steel knob was originally used rather than plastic knob 32, its wear during only one hour of rotation introduced enough iron and nickel into the pyrophosphate bath to significantly affect the morphology and mechanical properties of the copper deposit.

The invention provides a reproducible and convenient method for determining the tensile properties of deposits as illustrated by the following example.

EXAMPLE

Determining Tensile Properties of Copper Deposited From a Copper Pyrophosphate Bath Rotating cathode assembly 6 is fitted together by sliding end piece 20, cylinder cathode 16, and end piece 22 onto shaft 10, and securing them with threaded knob 32. Knurled nut 30 is then hand-tightened to seal shaft 10 from copper pyrophosphate plating bath 2. Assembly 6 is installed into rotator 12 and secured by a screw provided at the top of the rotator bearing assembly.

Anode assembly 8 is placed in cell 4, and cathode assembly 6 is lowered into its position within the anode, with knob 32 in depression 13 in bottom plate 14. When properly positioned, the cathode assembly is free to rotate.

During plating, cathode assembly 6 is rotated at 750 rpm. This rotation rate was chosen because it lies in the region of laminar flow. Consequently, the surface concentrations of solution species and the current density are both reproducible and uniform along the cathode surface. Deposition is thus performed under well-defined conditions so that the tensile properties of the deposit reflect the inherent bath characteristics.

Plating is continued until a band of suitable thickness is obtained. For tensile testing, a thickness of about 0.002 inch has proven satisfactory, although acceptable results have been obtained with bands ranging in thickness from 0.0004 to 0.005 inch.

Cathode 16 is removed from shaft 10 and the plated copper band removed from cathode 16. To facilitate this removal, the stainless steel cathode can be passivated before plating to form a uniform thin oxide layer so that a bond is not formed between the metal being deposited and the stainless steel cathode. Additionally, a cathode holder with a suitable diameter can be used so that the plated cylinder can be pressed off the cathode onto a slightly smaller diameter section of the holder.

Figure 3:
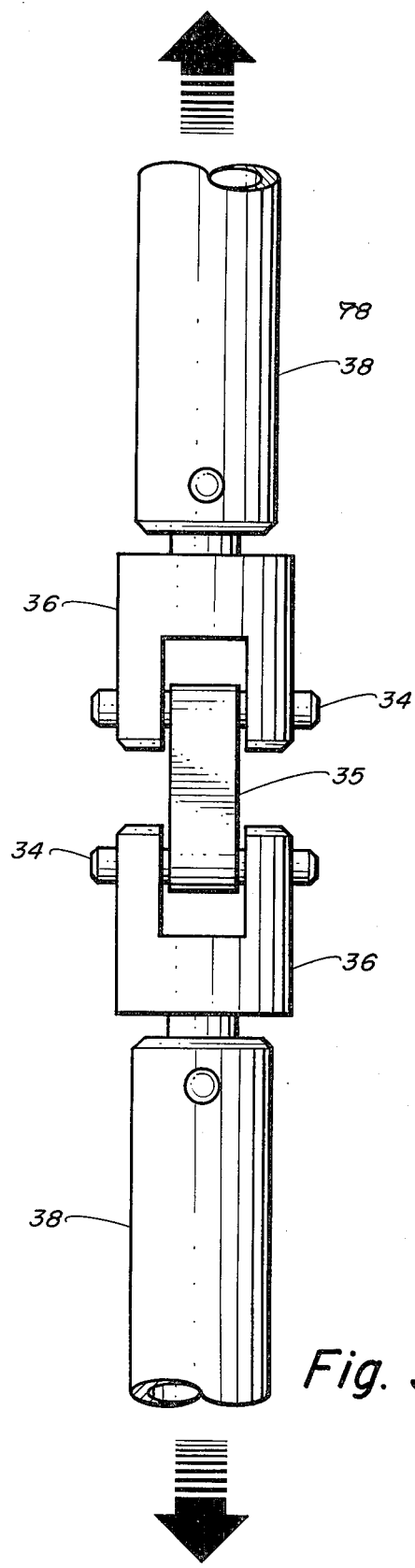
FIG. 3 is a perspective view of a clevis tensile fixture used to tensile test a band.

Bands are convenient for tensile testing because they can be readily held in a special clevis-type fixture. This fixture overcomes the slipping problem commonly encountered when conventional grips are used to hold thin foils. As shown in FIG. 3, a pair of pins 34 are inserted through band 35 and through the holes in a pair of clevises 36. Clevises 36 are fastened between pull rods 38 of a standard tensile test machine and stress-strain curves obtained in a conventional manner.

For some materials, and under some plating conditions, internal stresses in the deposit are high and the band cannot be slipped readily from the mandrel. In such cases, a soluble cathode, such as aluminum, can be used, and the cathode dissolved in a suitable solvent (e.g., 6 molar NaOH for aluminum) to separate it from the deposited band. If a soluble cathode is not used, a tight band can be removed by cutting it parallel to its axis and then peeling it off as a rectangular strip. The strip can then be tested in a conventional manner using standard tensile test grips. Such strips are not as convenient to test as bands, but they are reproducible because they are plated under precisely controlled conditions of solution mass transport.

In addition to being used to determine tensile properties, the method and bands of the invention can be used to determine the stress condition of a plated deposit. If a band springs open when it is cut, then the plated material was under a tensile stress. If a band tends to close or coil when it is cut, then the plated material was under a compressive stress. The degree of movement of the band after cutting is an indication of the amount of stress in the plated material. Thus, by comparing the diameter of the band before and after cutting, the type and relative amount of stress in the deposited material can be determined.

From the above example, one skilled in the art can readily make variations and modifications without departing from the invention. For example, the rotating electrode assembly can be used without an anode to deposit nickel bands from an electroless nickel bath. For some systems a simple flat anode rather than a ring anode may be used, although this will cause a cyclic variation in the plating current density as the cylindrical cathode rotates past the flat anode. The plating solution need not be contained in a beaker, but rather the anode and cathode assemblies can be placed in a production plating bath and the test band formed directly from the production bath. Accordingly, it should be clearly understood that the form of the invention described above and shown in the accompanying drawings is illustrative only and is not intended to limit the scope of the present invention.

What is claimed is:

1. A method of determining the tensile properties which can be obtained from a plating bath, comprising:
   providing a cylindrical cathode having removable insulating end pieces;
   supporting said cathode while completely immersed in a plating bath;
   rotating said cathode relative to the plating bath in which it is supported, whereby a band of metal is deposited on a surface of said cylindrical cathode between said end pieces;
   removing said cathode from said plating bath;
   removing said end pieces from said cathode;
   removing said band from said cathode;
   placing a pair of pins inside said band parallel to the axis of said band;
   holding each of said pins in a clevis-type tensile test fixture; and
   applying a tensile load to said band.

2. A method of determining the tensile properties which can be obtained from a plating bath, comprising:
   providing a cylindrical cathode having insulating end pieces;

supporting said cathode while completely immersed in a plating bath;

rotating said cathode relative to the plating bath in which it is supported, whereby a band of metal is deposited on a surface of said cylindrical cathode between said end pieces;

removing said cathode from said plating bath;

removing said band from said cathode;

forming a strip out of said band; and applying a tensile load to said strip.

3. The method as claimed in claim 1 or 2, wherein said deposit comprises an electroplated deposit, and said bath comprises an electroplating bath, and wherein said method further includes the step of providing an anode spaced from said cathode in said electroplating bath.

4. A method of determining the stress condition which can be obtained from a plating bath, comprising:

providing a cylindrical cathode having removable insulating end pieces;

supporting said cathode while completely immersed in a plating bath;

rotating said cathode relative to the plating bath in which it is supported, whereby a band of metal is deposited on a surface of said cylindrical cathode between said end pieces;

removing said cathode from said plating bath;

removing said end pieces from said cathode;

removing said band from said cathode;

cutting said band across its width; and measuring the change in diameter of said band after said cutting, whereby an increase in diameter indicates a tensile stress, and a decrease in diameter indicates a compressive stress in the deposit.

5. A method of determining the tensile properties which can be obtained from a plating bath, comprising:

providing a continuous cylindrical cathode having insulating end pieces;

supporting said cathode while completely immersed in a quiescent plating bath;

rotating said cathode relative to the plating bath at a speed which provides precisely controlled conditions of mass transport, whereby a band of metal is deposited on a surface of said cylindrical cathode between said end pieces;

removing said cathode from said plating bath;

removing said band from said cathode;

forming a strip out of said band; and applying a tensile load to said strip.

* * * * *